United States Patent [19]

Schuetz et al.

[11] Patent Number: 5,057,415

[45] Date of Patent: Oct. 15, 1991

[54] CONTINUOUS ENZYMATIC PROCESS FOR PREPARING PEPTIDES

[75] Inventors: Hans-Juergen Schuetz, Mettmann; Christian Wandrey, Juelich, both of Fed. Rep. of Germany

[73] Assignee: Forschungszentrum Juelich GmbH, Juelich, Fed. Rep. of Germany

[21] Appl. No.: 251,176

[22] Filed: Sep. 30, 1988

[30] Foreign Application Priority Data

Oct. 1, 1987 [DE] Fed. Rep. of Germany ....... 3733198

[51] Int. Cl.$^5$ ..................... C12P 21/00; C12N 11/08; C07K 01/06; C07K 01/14
[52] U.S. Cl. ................................. 435/68.1; 435/180; 435/288; 435/803; 435/813; 530/335; 530/338; 530/339; 530/344
[58] Field of Search ..................... 435/68.1, 174, 180, 435/288, 803, 813; 530/335, 338, 339, 344

[56] References Cited

U.S. PATENT DOCUMENTS

| | | | |
|---|---|---|---|
| 4,304,858 | 12/1981 | Wandrey et al. | 435/115 |
| 4,326,031 | 4/1982 | Wandrey et al. | 435/146 |
| 4,339,534 | 7/1982 | Johansen et al. | 435/70 |

OTHER PUBLICATIONS

Cramer et al., "Tandem Use of Carboxypeptidase Y Reactor and Displacement Chromatograph for Peptide Synthesis", Journal of Chromatography, 394 (1987) pp. 305–314.
Widmer et al., "Enzymatic Peptic Synthesis", Peptides 1982, Walter de Gruyter & Co. Berlin New York, 1983, pp. 375–379.
Fuganti et al., "Immobilized Penicillinacylase: Application to the Synthesis of the Dipeptide Aspartame", Tetrahedron Letters, vol. 27, No. 27, 1986, pp. 3191–3194.

*Primary Examiner*—David M. Naff
*Attorney, Agent, or Firm*—Foley & Lardner

[57] ABSTRACT

Peptide preparation is carried out by a continuous process by supplying a serine protease or peptidase enzyme retained in a reaction vessel with an alkyl ester of an N-protected amino acid or oligopeptide and a recycle stream containing an amino acid or oligopeptide to form an N-protected chain extended peptide, separating the N-protected chain extended peptide by adsorption on a hydrophobic absorbent, and eluting and recovering the adsorbed N-protected chain extended peptide. Adsorption is carried out without adjusting the pH from that in the reaction vessel, and adsorber effluent is recycled to the recycle stream. The protease or peptidase enzyme may be immobilized, and there is substantial exclusion of organic solubilizers in the reaction vessel. A preferred N-protecting group is an N-phenacyl group. The N-protecting group can be separated from the N-protected chain extended peptide with a deprotecting enzyme to recover the chain extended peptide. Apparatus is used that provides for continuous operation of the process.

27 Claims, 2 Drawing Sheets

CONTINUOUS ENZYMATIC PROCESS FOR PREPARING PEPTIDES

BACKGROUND OF THE INVENTION

The present invention relates to a substantially continuous enzymatic process for preparing optionally N-protected peptides, especially dipeptides, and to an apparatus for use therefor It is possible that di- and oligopeptides such as, for example, tyr-ala will in the future play an important part in parenteral nutrition: they cause a low osmolarity and are excellently water-soluble and thus can readily be used for infusion solutions. Furthermore, some peptides are distinguished by highly interesting pharmacological properties, such as, for example, the peptide hormones (for example tyr-arg). However, approval thereof as pharmaceutical agents requires high purity, especially enantiomeric purity above 99.9 ee. Such high enantiomeric purities can be achieved in conventional chemical processes only with great elaboration. Hence, enzymatic peptide synthesis Johansen et al., U.S. Pat. No. 4,339,534, the entire disclosure of which is incorporated herein by reference, discloses a process for the preparation of N-protected (N-acylated) dipeptides by enzymatic reaction of N-acylamino acid alkyl esters (A) with optionally C-protected amino acids (B) using carboxypeptidase as the enzyme, which can be in solution, insolubilized or immobilized on a carrier.

The examples in the Johansen patent reveal the utility of an organic solubilizer, e.g., an alcohol, in some cases, and the use of a large excess of amino acid relative to the ester. In addition, the reported results show a distinct improvement when the amino acid component B is used in the form of the amide and not as the free acid (which, however, makes an additional protective group removal necessary in order to obtain the peptide itself).

Detailed information on the elimination of the protective groups, especially of the N-acyl group, from the N-protected dipeptide is not provided in the Johansen patent.

The examples disclose a batchwise preparation with chromatographic fractionation of the reaction mixture at the end.

Further details of a procedure for the preparation of N-acyl-dipeptide amide taking the example of the reaction of N-acyl-arginine with methioninamide in the presence of immobilized carboxypeptidase (CPD) are given by Cramer et al., in J. Chromat., 394:305–314 (1987), who describe peptide synthesis in a fixed bed reactor with recycled reaction mixture and working-up of the product after sufficient reaction by displacement chromatography of the reaction mixture, which has been adjusted to pH 2.5 in an intermediate container, in batch operation.

The N-protective groups which are mainly exemplified in the abovementioned Johansen patent are benzoyl, acetyl and benzyloxycarbonyl from a plurality of groups stated to be possible. However, Widmer et al. ("Enzymatische Peptidsynthese" in "Peptides 1982" Walter de Gruyter & Co. Berlin New York, 1983, pages 375 to 379) disclose the use of the N-phenacetyl group as a protective group for the reaction of N-acyl-amino acid alkyl esters with amino acid amides in the presence of carboxypeptidase-Y (CPDY), and they indicate that it can be expected that the N-phenacetyl group could be enzymatically cleaved from small peptides using penicillin acylase.

Fuganti et al., Tetrahedron Letters, 27:3191–3194 (1986), disclose successful enzymatic deacylation of N-phenacetyl L,L-aspartame (N-phenacetyl L,L-aspartyl-phenylalanine methyl ester), a C-protected (esterified) N-phenacyldipeptide, using penicillin acylase immobilized on Eupergit. The phenacyl group was similarly but more slowly cleaved from N-phenacetyl L,L-aspartyl-valine methyl ester while the protective group was not eliminated from the N-acylated aspartic acid itself A need continues to exist for an economical and efficient process for synthesizing dipeptides and oligopeptides.

OBJECTS OF THE INVENTION

Accordingly, it is an object of the present invention to improve the economics of peptide synthesis.

Another object of the invention is to effect continuous enzymatic peptide synthesis with minimal enzyme consumption.

A further object of the invention is to avoid the need for an additional step to remove a C-protective group.

Yet another object of the invention is to develop an apparatus suitable for use in effecting efficient continuous enzymatic peptide synthesis.

SUMMARY OF THE INVENTION

These and other objects of the invention are achieved by providing a substantially continuous process for preparing a peptide, comprising the steps of:

(A) supplying to a reaction vessel, containing a serine protease or peptidase enzyme which is retained in the reaction vessel, a first aqueous phase reactant comprising an alkyl ester of a first N-protected amino acid or oligopeptide, and a second aqueous phase recycle stream comprising a second amino acid or oligopeptide, with substantial exclusion of organic solubilizers, said second amino acid or oligopeptide being present in sufficient excess and for a sufficient holdup time in said reaction vessel to substantially completely convert the first N-protected amino acid or oligopeptide ester to a mixture containing N-protected chain extended peptide and hydrolyzate;

(B) passing the effluent from the reaction vessel through a separating column containing a stationary phase comprising a hydrophobic absorbent, separating the resultant N-protected chain extended peptide and hydrolyzate from the reaction mixture by adsorption onto the adsorbent, and recycling the absorber effluent to step (A) as the recycle stream; and (C) eluting the adsorbed N-protected peptide with an aqueous eluent solution, and recovering an eluent stream comprising resultant separated N-protected chain extended peptide The process can include the step of removing the N-protecting group from the resultant separated N-protected chain extended peptide in the presence of a deprotecting enzyme, and recovering resultant chain extended peptide.

The invention further provides an apparatus for effecting substantially continuous peptide synthesis, comprising:

(A) an enzyme membrane reactor comprising an inlet and an outlet port and a reaction chamber, and containing a serine protease or peptidase enzyme in said reaction chamber;

(B) at least two columns, each of which is provided with an inlet port and an outlet port and is charged with a hydrophobic adsorbent for separating N-protected chain extended peptide from the effluent stream from said enzyme membrane reactor; wherein each such column is provided with means for alternately (i) directing to the inlet port thereof effluent from said enzyme membrane reactor, and directing effluent from the outlet port thereof to a recycle circuit which communicates with said enzyme membrane reactor inlet port, or (ii) directing to the inlet port thereof aqueous eluent solution for desorbing separated N-protected chain extended peptide, and directing effluent from the outlet port thereof to a deprotecting reaction vessel; and (C) a deprotecting reaction vessel provided with an inlet port in selective communication with the outlet port of each of said at least two columns, and an outlet port, and charged with a deprotecting enzyme for cleaving said N-protecting group, said enzyme being retained in said vessel.

DETAILED DESCRIPTION

Figure 1:
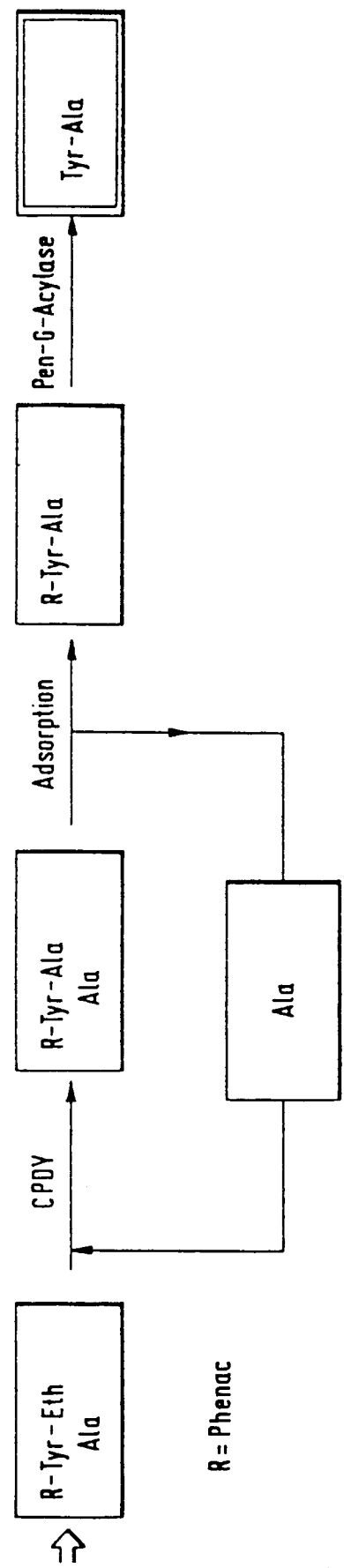
FIG. 1 is a reaction diagram for an illustrative process according to the invention.

The process which has been developed according to the invention for this purpose is of the type specified in the introduction and comprises the reaction being carried out continuously, with the exclusion of organic solubilizers, and with retention of the enzyme in the reaction chamber, with such an amino acid excess and such a holdup time which results in the quantitative conversion of the amino acid ester, which comprises the N-protected peptide being separated, by adsorption to a hydrophobic adsorber, from the reaction mixture which leaves the reaction chamber and is returned for the conversion, and which comprises finally, the protective group being cleaved enzymatically, where appropriate, from the N-protected peptide which has been eluted from the adsorber with aqueous solution. It is possible in this way to obtain optionally N-protected dipeptides or oligopeptides in an economical fashion.

In the process according to the invention, the serine protease or peptidase enzyme used in step (A) is advantageously employed in a form which ensures its retention in the reaction vessel, e.g., immobilized on a carrier or retained in an enzyme membrane reactor (EMR).

Any of the many known, conventional carriers for immobilized enzymes can be used as carrier for the protease/peptidase enzyme. It will generally be a high molecular weight material with reactive groups for coupling with groups on protein molecules. An especially preferred carrier is oxirane activated acrylic beads, e.g., Eupergit (Rohm Pharma., Darmstadt, W. Germany). Immobilization is effected by conventional methods, e.g., glutaraldehyde linkage or reaction of functional groups on the enzyme, e.g., amine, carboxylate and the like, with reactive functions on the carrier, e.g., oxirane, halogens, anhydrides and the like.

Suitable EMRs include any of the conventional reactors with a membrane capable of retaining the enzyme. Generally, membranes based on cellulose acetate are useful, having a cut-off that will ensure retention of molecules of the size of the enzyme to be used therein. The cut-off for CPD's such as CPDY is about 5,000, and a cut-off of about 5,000 is used for a deprotecting enzyme such as penicillin G acylase as well. Preferred EMRs include those described in, e.g., U.S. Pat. Nos. 4,304,858 and 4,326,031, the entire disclosures of which are incorporated herein by reference.

The molar ratio of amino acid or oligopeptide to N-protected amino acid or oligopeptide ester is advantageously greater than 50:1, preferably at least about 200:1, depending upon the particular components to be reacted. When reacting alanine with N-phenacetyl tyrosine methyl ester, a ratio of about 500:1 was favorably used. Higher ratios can be used, but little benefit is realized.

The enzyme used for the peptide formation step can be any peptidase, preferably an exopeptidase, and is advantageously a carboxypeptidase, e.g., one of those described in the aforementioned Johansen patent, preferably carboxypeptidase Y (from yeast fungi), which is readily available commercially Suitable N-protecting groups include any of the conventional groups, e.g., those described in the Johansen patent, advantageously an acyl group, and preferably a phenacetyl group. Preferred reactants are N-phenacetyl amino acid alkyl esters, although N-protected oligopeptide, preferably dipeptide, tripeptide or tetrapeptide, alkyl esters can also be used. Alkyl esters are advantageously lower alkyl, preferably $C_1$-$C_4$ alkyl esters.

Preferred N-protected amino acid esters for use in the process of the invention include lower alkyl esters, preferably N-phenacetylamino acid $C_1$-$C_4$ alkyl esters of aromatic amino acids and, more preferably, N-phenacetyltyrosine lower alkyl esters (especially $C_1$-$C_4$ alkyl esters).

The free amine component can be any amino acid or oligopeptide with a free N-terminal amine. Amino acid are preferred over oligopeptides and short oligopeptides, especially di-, tri- or tetrapeptides, are preferred over long ones. Preferred amino acids for use in the process of the invention include alanine, serine, glycine, methionine, isoleucine, valine, leucine and arginine, and especially alanine.

Conditions for the enzymatic peptide formation reaction will generally be conventional for reaction in aqueous solution, and will normally be analogous to those disclosed in the above-referenced Johansen patent. The temperature, pH and holdup time in the reaction vessel will be selected to optimize the rate of ester aminolysis (peptide formation) and minimize ester and peptide hydrolysis and enzyme denaturation. Generally, the temperature will be in the range of 5°–50° C., advantageously close to room temperature, e.g., about 20° C. The pH is normally slightly alkaline to favor esterase activity relative to peptidase activity, which is higher at slightly acidic pH, advantageously in the range of 7–10, preferably about 8.4 for CPDY and related carboxypeptidases.

The separation step is generally effected in a column containing the hydrophobic adsorbent, although any conventional vessel can be used. Suitable hydrophobic adsorbents include any adsorbent capable of selectively binding an N-protected, preferably N-phenacyl, di- or oligopeptide and efficiently separating it from an aqueous solution. Polystyrene beads, e.g., Amberlite XAD-2 (Rohm & Haas, Philadelpia, Pa.), is especially useful for removing the N-protected (di)peptide which is formed from the reaction mixture One advantage of such an adsorbent is that it separates and retains the N-protected peptide without the need to adjust the pH of the effluent from the first enzyme reactor and permits facile recirculation of the adsorber column effluent, containing unreacted amino acid or oligopeptide, to the peptide synthesis reactor.

For continuous operation, it is expedient to use at least two adsorber columns in tandem, alternately feeding the peptide reactor effluent to one column and recirculating the effluent to the reactor, while eluting the other column and recovering the N-protected chain extended peptide, which can then be deprotected, and then readjusting the pH of the adsorbent to receive peptide reactor effluent again. The aqueous effluent from the column, while it is receiving peptide reactor effluent, is recycled to the peptide reactor, normally with intermediate stripping of the alcohol resulting from esterolysis. This is advantageously effected by gas stripping, e.g., by passage of an inert gas such as nitrogen or helium through the solution.

The eluent for recovery of the separated N-protected peptide (and N-protected hydrolyzed reactant which has lost the ester alkyl group) is advantageously a washing solution of dilute aqueous acid, e.g., hydrochloric acid, followed by dilute aqueous alkali solution, e.g., dilute alkali metal hydroxide such as NaOH, KOH and the like. The elution effluent is adjusted to the pH for deprotection, if desired, e.g., with dilute acid, and fed to the deprotection step. The adsorber is also advantageously adjusted to the pH of the peptide reactor effluent for subsequent reuse in the separation step.

The deprotecting enzyme is selected according to the nature of the N-protecting group. For N-acyl protecting groups, an acylase enzyme is advantageously used. For the enzymatic elimination of the N-phenacyl protective group, penicillin G acylase is preferred. The enzymatic deprotection reaction is advantageously effected substantially continuously, preferably in a reactor with means to retain the deprotecting enzyme therein, e.g., an EMR or a vessel which can retain a carrier on which the enzyme is immobilized.

Conditions for the deprotection reaction will be conventional for the enzyme used, and will be chosen to maximize cleavage of the N-protecting group and minimize hydrolysis of the peptide and denaturation of the enzyme. For acylases such as penicillin acylase, a pH range of 7 to 8.5 is advantageously used, preferably a pH of about 7.5, and a temperature range of 5°–50° C., preferably near room temperature, e.g., about 20° C.

Specific investigation has been carried out of L,L-dipeptide formation between a readily soluble aliphatic and a poorly soluble aromatic amino acid taking the example of tyrosine, alanine, viz.:

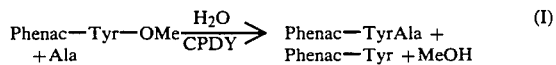
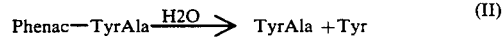
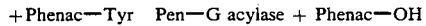

The above mentioned reactions take place in aqueous phase and were carried out continuously.

The peptide formation (I) was carried out both in an EMR and with an enzyme immobilized on a carrier. The enzyme used was CPDY supplied by Carlbiotech. Eupergit (an acrylic bead polymeric carrier activated with oxirane rings) was used for the immobilization. Holdup times down to below 10 minutes were employed and were determined beforehand depending on the enzyme concentration. The loss of enzyme activity amounted to about 0.7%/d. It emerged that the selectivity of the reaction with homogeneous catalysis (in the enzyme membrane reactor) was slightly raised (by 5 to 10%).

The N-acylated dipeptide obtained in the reaction (I) was removed from the reaction mixture by adsorption onto a hydrophobic absorber such as, for example, Amberlite XAD-2, onto which the N-acyl-dipeptide was adsorbed from the EMR discharge without any pH change being necessary. For continuous operation it is expedient to use two Amberlite columns in turns, to one of which the EMR discharge is applied, while the N-acyl-dipeptide accumulated in phase 1 is eluted from the other. The amino acid used in large excess is not retained by the adsorber and is returned to the peptide reactor.

The elimination of the protective group (reaction II) with penicillin G acylase is expediently carried out at pH values of 7 to 8.5, especially about 7.5. This reaction can also be carried out both with enzyme immobilized on a carrier and in homogeneous phase in an EMR. Reaction with enzyme immobilized on Eupergit has proved particularly suitable. The resulting dipeptide can be obtained from the reaction mixture and purified, for example by crystallization.

Figure 2:
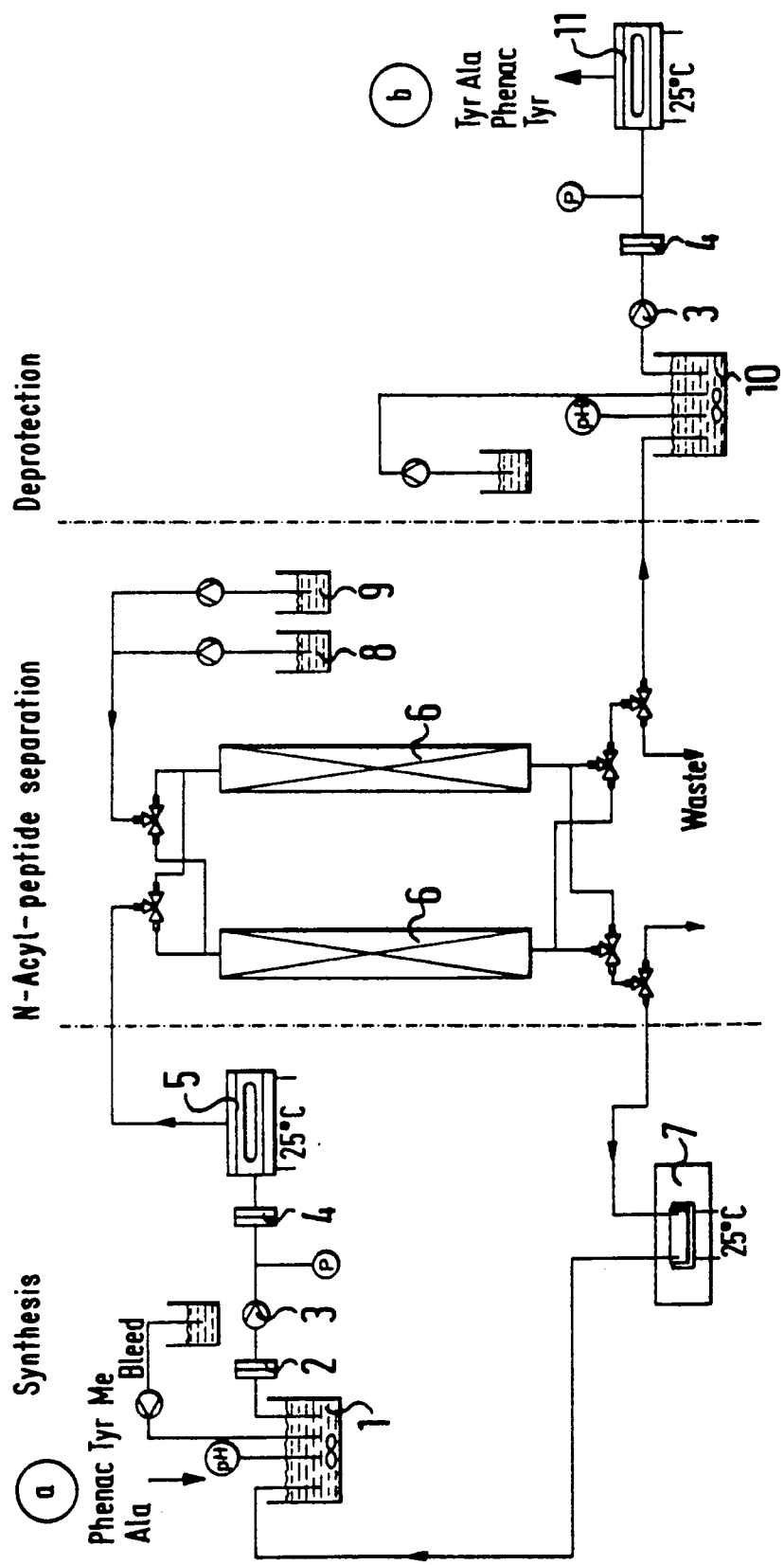
FIG. 2 is a symbolic representation of an illustrative apparatus suitable for effecting the process according to the invention.

The attached drawings illustrate the reaction which is carried out, in this case with the ethyl ester, and the apparatus for effecting the reaction FIG. 1 shows a reaction diagram for a typical reaction FIG. 2 shows a diagram for one embodiment of a continuously operating apparatus for dipeptide preparation.

The apparatus depicted in FIG. 2 with inlet at a and outlet at b comprises a balancing and substrate storage vessel 1 which is charged with starting material and receives recycled alanine (after removal of the ethanol by gas stripping if necessary, not shown). A metering pump 3 pumps reaction liquid from the latter via a primary filter 2 and via a sterile filter 4 into the enzyme membrane reactor 5, which operates at 25° C., for the peptide synthesis.

The discharge from the reactor passes via one of the columns 6 which are operated alternately for removal of product and where the N-acyldipeptide which is formed is collected on the column until breakthrough, while the alanine which is present in the discharge from the column runs back to the outlet via a polarimeter 7, with the aid of which the residual alanine concentration is determined. The substrate storage vessel 1 can be furnished with a gas inlet and a downstream outlet for the stripping gas and the gaseous stream containing such gas and entrained alcohol, respectively.

Washing liquid (dilute hydrochloric acid) is pumped from a storage vessel 8, after the columns have been changed over, into the completely loaded column, and subsequently eluent (dilute NaOH) from 9.

The adsorber effluent enters the vessel 10 which acts as a balancing vessel and in which the pH is adjusted to the range suitable for the deacylation.

The pump and sterile filter are in turn labeled 3 and 4, respectively. P are pressure sensors. The deacylation finally takes place in the enzyme membrane reactor 11 at 25° C., and from its discharge it is possible to separate the dipeptide without difficulty from the phenylacetic acid which is present, and from the tyrosine which derives from the hydrolysis in stage I of the synthesis, by selective adsorptions or crystallization.

The process according to the invention is further illustrated by the following detailed example which, however, is not limitative thereof

EXAMPLE

A 10 ml EMR was operated with 1 mg of CPDY at 25° C. The holdup time was 10 minutes. The concentration of the substrate solution corresponded to 2 mM phenac-tyr-OMe and 1 M alanine. Its pH was 8.4. The product solution drawn off from the EMR contained 65% N-acylated dipeptide and 35% hydrolysate N-phenac-tyr (based on the ester employed) with a space-time yield of 50.6 g/l-d. The loss of enzyme activity was 0.7% per day, i.e., 3.4 mg of enzyme were consumed per kg of dipeptide. The N-acyl dipeptide was removed by adsorption on Amberlite XAD-2. The unreacted alanine was again mixed with phenac-tyr-OMe and returned to the reactor.

The adsorbed N-acyl-dipeptide was desorbed from the Amberlite using 50 mM NaOH, the pH of the solution was adjusted to 7.7 with dilute HCl, and the phenac protective group was eliminated in aqueous solution with the aid of penicillin G acylase immobilized on Eupergit (10 mg of enzyme/1 g of Eupergit) at 25° C. The elimination was complete when the holdup time in the column was 55 min. The holdup time is normally selected in the range 40–70 min, it being necessary to avoid excessively long holdup times because of the then increasing hydrolysis of the dipeptide. It was possible to achieve holdup times in the enzyme membrane reactor down to 10 min with comparable enzyme concentrations.

The phenylacetic acid contained in the discharge was removed from the product solution by absorption on Amberlite XAD-2.

Working-up was by fractional crystallization. The optical purity of the resulting dipeptide was greater than 99 ee (detection limit).

As an alternative, the deacylation was carried out in an enzyme membrane reactor: for this, a 2 mM N-acyl-dipeptide solution (discharge from the Amberlite XAD-2 column) was adjusted to pH 7.8 and pumped, with a holdup time of 15 min, through a 10 ml EMR with a membrane with a cutoff of 5,000. The reactor contained 20 mg of penicillin G acylase. The maximum conversion was 85%. The loss of enzyme activity was 1.3% per day.

Although the preparation of free dipeptides is mainly described hereinbefore, it is of course also possible according to the invention to obtain N-protected peptides or dipeptides which may be of interest as intermediates or else, where appropriate, themselves endowed with their own pharmacological action.

Of course, for the p reparation of oligopeptides, free peptide will be used in place of the free amino acid and/or an N-protected peptide ester will be used in place of the N-protected amino acid ester. Other variations in the reactants and conditions, as well as in the apparatus used to effect the process of the invention, will be apparent to the ordinary skilled artisan for practising the invention in its broadest scope.

What is claimed is:

1. A continuous process for preparing a peptide, comprising the steps of:
(A) supplying to a reaction vessel, containing a serine protease or peptidase enzyme which is retained in the reaction vessel, a first aqueous phase reactant comprising an alkyl ester of a first N-protected amino acid or oligopeptide, and a second aqueous phase recycle stream comprising a second amino acid or oligopeptide, with substantial exclusion of organic solubilizers, said second amino acid or oligopeptide being present in sufficient excess and for a sufficient holdup time in said reaction vessel to substantially completely convert said first N-protected amino acid or oligopeptide ester to a mixture containing N-protected chain extended peptide and hydrolyzate, said conversion being at a first pH;
(B) passing the mixture containing the N-protected chain extended peptide and hydrolyzate from said reaction vessel through a separating column containing a stationary phase comprising a hydrophobic adsorbent without adjusting the pH of the mixture, separating the N-protected chain extended peptide and hydrolyzate from the mixture by adsorption onto said adsorbent, and recycling adsorber effluent to step (A) as said recycle stream; and
(C) eluting the adsorbed N-protected peptide with an aqueous eluent solution at a second pH, and recovering an eluent stream comprising the N-protected chain extended peptide formed in step (A) wherein the N-protecting group is a N-phenacyl group.

2. The process of claim 1, which further comprises the step of:
(D) removing the N-protecting group from said resultant separated N-protected chain extended peptide in the presence of a deprotecting enzyme, and recovering resultant chain extended peptide.

3. The process of claim 2, wherein step (D) is effected continuously by passing the aqueous eluent stream from step (C) comprising separated N-protected chain extended peptide through a second reaction vessel containing said deprotecting enzyme in a form which ensures its retention in said vessel, with a holdup time sufficient to substantially completely cleave said N-protecting group, and recovering the resultant effluent stream comprising said chain extended peptide.

4. The process of claim 1, wherein said first aqueous phase comprises the N-protected amino acid alkyl ester.

5. The process of claim 1, wherein said second aqueous phase comprises the amino acid.

6. The process of claim 4, wherein said second aqueous phase comprises the amino acid.

7. The process of claim 2, wherein said deprotecting enzyme is penicillin G acylase.

8. The process of claim 1, wherein N-phenacyl amino acid alkyl ester is an ester of an aromatic amino acid.

9. The process of claim 8, wherein said aromatic amino acid is tyrosine.

10. The process of claim 5, wherein said amino acid is alanine, serine, glycine, methionine, isoleuciune, valine, leucine or arginine.

11. The process of claim 10, wherein said amino acid is alanine.

12. The process of claim 1, wherein said serine protease or peptidase enzyme is a carboxypeptidase.

13. The process of claim 12, wherein said carboxypeptidase is carboxypeptidase Y.

14. The process of claim 1, wherein said serine protease or peptidase enzyme is immobilized on a carrier.

15. The process of claim 14, wherein said carrier is oxirane activated acrylic beads.

16. The process of claim 1, wherein said reaction vessel in step (A) is an enzyme membrane reactor, said serine protease or peptidase enzyme being retained therein.

17. The process of claim 1, wherein said hydrophobic adsorbent in step (B) is polystyrene beads.

18. The process of claim 1, wherein said recycle stream contains alcohol and the alcohol is stripped from said recycle stream with an inert gas.

19. The process of claim 1, wherein the molar ratio of said amino acid or oligopeptide to said N-protected amino acid or oligopeptide alkyl ester is at least about 200:1.

20. The process of claim 17, wherein said ratio is about 500:1.

21. The process of claim 3, wherein said deprotecting enzyme is penicillin G acylase, and wherein said enzyme is immobilized on a carrier.

22. The process of claim 21, wherein the pH in said second reaction vessel is in the range 7.0–8.5.

23. The process of claim 21, wherein said carrier is oxirane activated acrylic beads.

24. The process of claim 1, wherein at least two separating columns are used in tandem in steps (B) and (C), at least one of which receives the mixture from step (A) for separation, wile at least one other of which receives said aqueous eluent solution and produces said eluent stream comprising resultant separated N-protected chain extended peptide.

25. The process of claim 1, wherein said N-protecting group is removed at a pH that is lower than said first pH.

26. The process of claim 1, wherein the pH of the eluent stream from step (C) is adjusted and the stream is fed to a reactor containing a deprotecting enzyme to remove the N-protecting group.

27. The process of claim 1, wherein the adsorber effluent in step (b) contains alcohol and the alcohol is stripped from the effluent before the effluent is recycled to step (A).

* * * * *